(12) United States Patent
Achatz et al.

(10) Patent No.: US 8,399,200 B2
(45) Date of Patent: Mar. 19, 2013

(54) ISOLATION OF ALLERGEN-SPECIFIC IMMUNOGLOBULIN GENES FROM HUMAN B-CELLS FROM ATOPY SUFFERERS

(75) Inventors: Gernot Achatz, Salzburg (AT); Michael Huhn, Leverkusen (DE); Rainer Fischer, Monschau (DE); Fatima Ferreira, Salzburg (AT); Elke Luger, Marchtrenk (AT); Michael Stöcker, Aachen (DE); Stefan Barth, Roetgen (DE); Torsten Klockenbring, Bonn (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 1329 days.

(21) Appl. No.: 11/597,492

(22) PCT Filed: May 25, 2005

(86) PCT No.: PCT/EP2005/052398
§ 371 (c)(1),
(2), (4) Date: Aug. 17, 2007

(87) PCT Pub. No.: WO2005/116645
PCT Pub. Date: Dec. 8, 2005

(65) Prior Publication Data
US 2010/0035241 A1 Feb. 11, 2010

(30) Foreign Application Priority Data
May 26, 2004 (EP) .................................. 04012408

(51) Int. Cl.
*C12Q 1/68* (2006.01)

(52) U.S. Cl. ..................................................... 435/6.14

(58) Field of Classification Search ........................ None
See application file for complete search history.

(56) References Cited

FOREIGN PATENT DOCUMENTS
WO WO 92/01047 1/1992

OTHER PUBLICATIONS

Wang et al. (J. Immuno. Meth. 2000, vol. 244, No. 1-2, p. 217-225).*
Nakamura et al. (J. Immunol., 1988, 4165-4172).*
Weitkamp et al. (J. Immunological Methods, 2003, 275 (p. 223-237).*
Lieby et al. (Blood, 2001, 97(12):3820-2828, IDS.*
Wang et al. (J. Immunological Methods, 2000, 244, p. 217-225).*
Hoon et al. (Cancer Research, 1993, 53:5244-5250).*
Luger et al. (Eur. J Immunol., 2001, 31:2319-2330, IDS reference).*
Lieby et al., "The clonal analysis of anticardiolipin antibodies in a single patient with primary antiphospholipid syndrome reveals an extreme antibody heterogeneity", Blood, vol. 97, No. 12, pp. 3820-3828, Jun. 2001.
Wang et al., "Human immunoglobulin variable region gene analysis by single cell RT-PCR", Journal of Immunological Methods, vol. 244, pp. 217-225, Oct. 2000.
De Wildt et al., "A new method for the analysis and production of monoclonal antibody fragments originating from single human B cells", Journal of Immunological Methods, vol. 207, pp. 61-67, Aug. 1997.
Feuchtenberger et al., "Semiquantitative and qualitative assessment of B-lymphocyte $V_H$ repertoire by a fluorescent multiplex PCR", Journal if Immunological Methods, vol. 276, pp. 121-127, May 2003.
Rassenti et al., "Analysis of immunoglobulin $V_H$ gene repertoire by an anchored PCR-Elisa", Annals New York Academy of Science, pp. 463-473, Jul. 1994.
Huse et al., "Generation of a large combinatorial library of the immunoglobulin repertoire in phage lambda", Science, vol. 246, No. 4935, pp. 1275-1281, Dec. 1989.
Ward et al., "Binding activities of a repertoire of single immunoglobulin variable domains secreted from *Escherichia coli*", Nature, vol. 341, No. 6242, pp. 544-546, Oct. 1989.
Barth et al., "Construction and in vitro evaluation of RFT5(scFv)-ETA', a new recombinant single-chain immunotoxin with specific cytotoxicity towards CD25+-Hodgkin-derived cell lines," Int. J. Mol. Med. 1:249-256 (1998).
Barth et al., "Ki-4(scFv)-ETA', a new recombinant anti-CD30 immuntoxin with highly specific cytotoxic activity against disseminated Hodgkin tumors in SCID mice," Blood, 95(12):3909-3914 (2000).
Barth et al., "Recombinant anti-CD25 immunotoxin RFT5(scFv)-ETA' demonstrates successful elimination of disseminated human Hodgkin lymphoma in SCID mice," Int. J. Cancer 86:718-724 (2000).
Dower et al., "High efficiency transformation of *E. coli* by high voltage electroporation," Nucleic Acids Res. 16 (13):6127-1645 (1988).
Hansen et al., "Inhibition of metalloproteinases enhances the internalization of anti-CD30 antibody Ki-3 and the cytotoxic activity of Ki-3 immunotoxin," Int. J. Cancer 98:210-215 (2002).
Klimka et al., "An anti-CD30 single chain Fv selected by phage display and fused to *Pseudomonas* exotoxin A (Ki-4(scFv)-ETA') is a potent immunotoxin against Hodgkin-derived cell line," Br. J. Cancer 80(8):1214-1422 (1999).
Klimka et al., "Human anti-CD30 recombinant antibodies by guided phage antibody selection using cell panning," Br J Cancer 83(2):252-260 (2000).

(Continued)

*Primary Examiner* — Stephanie K Mummert
(74) *Attorney, Agent, or Firm* — Dardi & Herbert, PLLC; Curtis B. Herbert

(57) ABSTRACT

A process is disclosed which enables the establishing of comprehensive immunoglobulin-specific reaction profiles of subjects with disorders of the immune function by the individual V gene repertoire of Ig-expressing B cells. The process comprises the isolation of B cells from body fluids, the isolation of individual B cells and their genetic material, the amplification of nucleic acids coding the variable regions of an antibody expressed by a B cell, the recombinant preparation of antibodies by expressing the amplificates, and the determination of the binding capability of the recombinant antibody to antigens.

12 Claims, 5 Drawing Sheets

OTHER PUBLICATIONS

Luger et al., "Somatic diversity of the immunoglobulin repertoire is controlled in an isotype-specific manner," Eur. J. Immunol. 31:2319-2330 (2001).

Matthey et al, "Recombinant immunotoxins for the treatment of Hodgkin's disease (Review)," Int. J. Mol. Med. 6:509-514 (2000).

Mudde et al., "Antigen presentation in allergic sensitization," Immuol. Cell Biol. 74: 167-173 (1996).

Tur et al., "Selection of scFv phages on intact cells under low pH conditions leads to a significant loss of insert-free phages," BioTechniques 30:404-413 (2001).

Vercelli et al., "To E or not to E? Can an IL-4-indiuced B cell choose between IgE and IgG4?," Int Arch Allergy Immunol 116:1-4 (1998).

* cited by examiner

ISOLATION OF ALLERGEN-SPECIFIC IMMUNOGLOBULIN GENES FROM HUMAN B-CELLS FROM ATOPY SUFFERERS

RELATED APPLICATION

This application claims priority to PCT Application No. PCT/EP2005/052398 filed May 25, 2005, which claims priority to European Patent Application No. 04012408.3 filed May 26, 2004, each of which are hereby incorporated herein by reference.

TECHNICAL FIELD OF THE INVENTION

The invention relates to a process for determining the immunological reaction profile of an organism. The invention further relates to the RT and PCR products obtainable by the above mentioned process, and to the vectors containing said RT and PCR products. In addition, the invention relates to the use of such vectors for the preparation of recombinant antibodies, and to such recombinant antibodies, as well as to the use of such recombinant antibodies in the above mentioned process for analyzing their binding activity.

BACKGROUND OF THE INVENTION

Type I supersensitivity reactions are characteristic of atopic diseases. In terms of pathophysiology, the disease is attributed to disorders of immunological tolerance mechanisms, which have not been clarified in detail. The underlying immune reactions are mostly directed against harmless antigens that are tolerated by healthy subjects. These inflammation reactions are mediated by class E immunoglobulins. The IgE molecules are bound by mast cells and basophilic granulocytes through surface receptors. If, upon antigen contact, cross-linking between IgE/IgE receptor complexes occur, processes which lead to secretion of inflammation mediators are induced in the cells concerned. This is the starting point of the wide variety of symptoms observed in atopic diseases.

A humoral immune response begins with an IgM dominated primary antibody response. Later on, the antibody repertoire becomes specified by a switch recombination to the antibody isotypes IgG, IgA or IgE. These antibody classes are also employed for "memory antibodies" later. Having a higher affinity for a particular antigen is characteristic of the antibodies of the secondary immune response. The phenomenon on which this development is based is referred to as "affinity maturation of the antibody repertoire". It is achieved by somatic mutations in the hypervariable regions of the variable regions of the heavy and light antibody chains and takes place within the germinal centers of lymphatic organs. The producers of the immunoglobulins are B lymphocytes whose maturation, differentiation and clonal expansion are essentially determined by the mutual contact with antigen-presenting cells and T helper (Th) cells. Thus, each B cell lineage expresses only one, genetically unique, variant of an immunoglobulin. Thus, the variability of different binding specificities is determined by the repertoire of different clonal origin cells. The mutual ratio of the sizes of the individual clones is determined by the dynamic adaptation to the current requirements. The specific binding activity towards antigens is established by the constitution of the variable regions of the light and heavy chains of an antibody.

Type 2 Th cells have a major influence on the development of IgE-secreting plasma cells. The orientation of immunological processes towards a particular antigen is ensured by highly specific surface receptors (B cell receptor, T cell receptor) on the B and Th lymphocytes, which enables the initial contact of both cell types only in the presence of an antigen for which both must have a specific receptor. This antigen-specific orientation of the immune reaction can be lost at high IgE titers when B cells of quite different specificities bind soluble immunoglobulins of these classes through the low-affinity receptor for IgE (CD23), and thus, in addition to their original specificity represented by the membrane-bound B cell receptor, recognize and internalize IgE-specific antigens and come into antigen-specific contact with Th2 cells through MHC II molecules. Thus, consequently, further IgE-secreting plasma cells are formed which can extend the hypersensitive antigen range extremely [1].

Although the participation of individual immunoglobulin classes in the atopic events has been described [2], the functional relationships between different classes of antibodies within the immune system, their influences on the overall structure, for example, within the scope of physiological and pathophysiological processes (such as atopic diseases, but also autoreactive reactions, sepsis, tolerance and anergy-controlling processes), are insufficiently understood. More profound insights into these processes can be derived from differentiated reaction profiles of the B cell lineages involved in the events, which may provide an image of the influence on the range of the antigen-specific V gene and antibody repertoires and isotype pattern in a functional relationship with the immunophysiological and pathophysiological status. To date, the enormous variability of the antibody repertoire has been a critical obstacle to the preparation of high-resolution representative reaction profiles.

Limited antigen-specific reaction profiles of antibodies are performed on the basis of serum analyses. Thus, the blood serum can be examined for reactivity against about 600 different allergens. However, this method does not provide any information about non-secreting B cells which are inhibited from secreting antibodies by suppressive influences. Thus, not all potentially reactive cells are covered, and it is not possible with this method to determine the presence of a predisposition for immune diseases.

Further, it is possible to determine the antigen-specific reaction profile directly at the patient, in vivo, by skin prick, intracutaneous and challenge tests. These methods have drawbacks in that they put a load on the patient and can be applied only to a limited extent with highly allergic subjects.

Antigen-specific V gene profiles based on single cell analyses have also been described [3, 4]. These approaches are suitable for a representative portrayal of the antigen-specific V gene repertoire, but have not been used for a comprehensive isotype-specific analysis of the V gene repertoires in this form.

Recently, also in the mouse model system, B cells which are undergoing the affinity maturation process (somatic hypermutation) could be successfully isolated. A protocol was developed which enabled the subsequent isolation of B cells by means of FACS. From the hapten- or allergen-specific cells, RNA was isolated and subsequently subjected to reverse transcription into cDNA. Subsequently, allergen/hapten-specific heavy chains of immunoglobulins could be isolated from the cDNA by means of RT-PCR. The sequences were then subjected to an intensive computer analysis. The following results were achieved:

Without any doubt, the IgE response is able to "mature".
The somatic diversity is different from isotype to isotype.
The antigen receptor is necessary for the selection of high affinity antibodies.
The antigen receptor has no function for the regulation of the somatic mutation process.

The shorter the CDR3 region, the higher the affinity of the antibodies for the hapten.

IgE does not form any "long lived" plasma cells.

The IgE response has a short life.

The cytoplasmic "tail" seems to be a suitable target for allergy therapy.

The results of this partial project have been published in the "European Journal of Immunology" [5].

Thus, due to the enormous variability of the antibody repertoire, it has been problematic or impossible to determine a comprehensive antigen-specific reaction profile of an organism. In particular, there has been no low risk method that puts a low load on the patient for evaluating their allergic (antigen-specific) reaction profile. Surprisingly, the present invention offers a solution to this problem. The subject matter of the invention of the present application allows the antigen-specific reaction profile of an organism to be determined on a genetic level. Surprisingly, it is possible in this way to cover all B-cell-mediated antigen-specific reactions, especially including those in which the secretion activity of the B cells is inhibited by suppressive influences.

DETAILED DESCRIPTION

Figure 1:
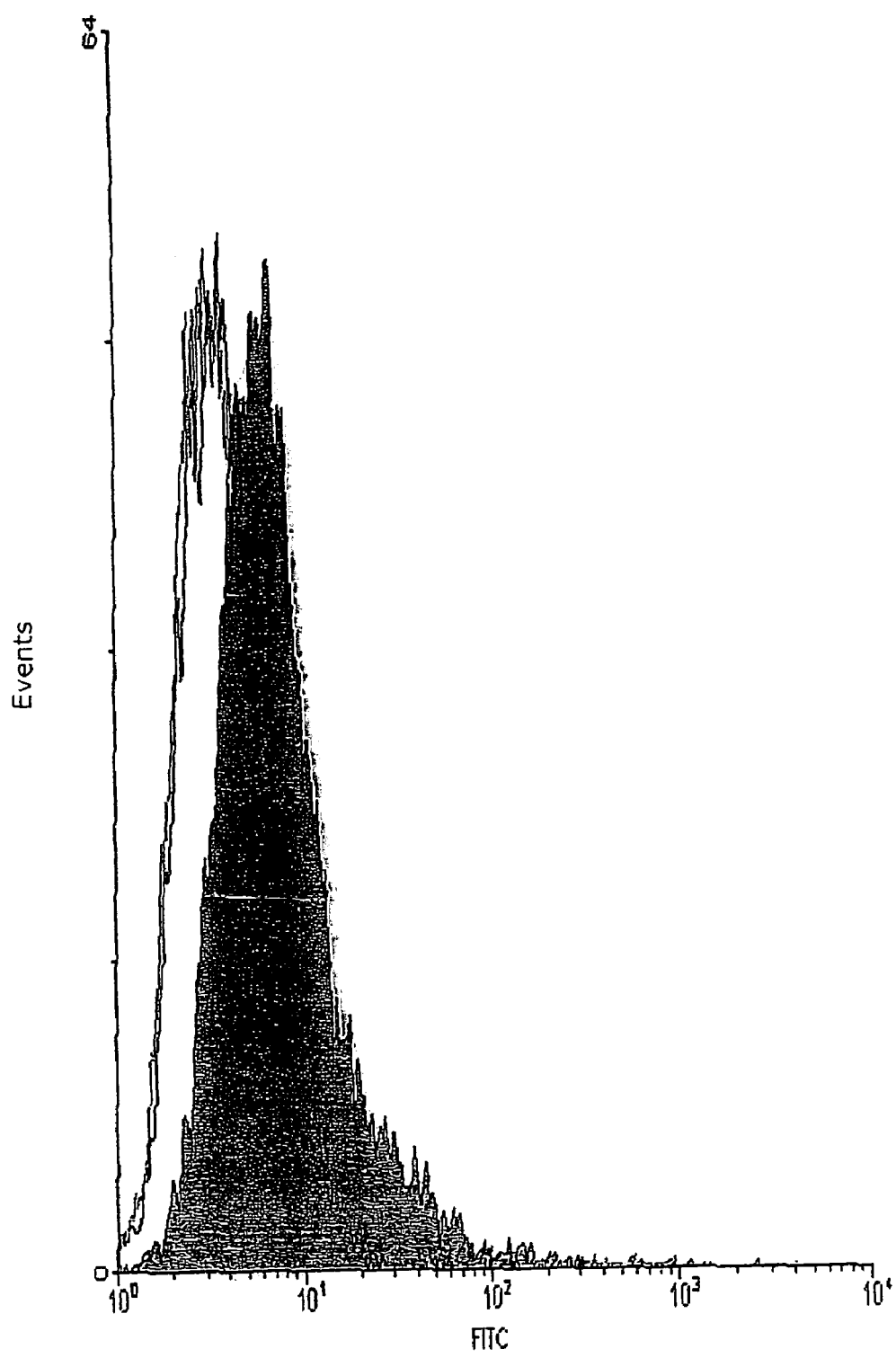
FIG. 1: FACS analysis of EBV-transformed human B cells which were selected against the timothy grass allergen Phl pVb. The specific binding to LPV-ETA' by an EBV-transformed B cell line (solid curve) derived from an antigen-specific selection process is shown. LPV-ETA' is a fusion protein consisting of the recombinant allergen Phl p5b and the modified enterotoxin A from *Staphylococcus aureus*. Binding activities directed against the toxin fragment were examined with a control antigen HAI-ETA', a fusion protein consisting of an antibody fragment and the above mentioned enterotoxin A domain (open curve). Non-specific reactions which occur as a background of the measurements by using secondary detection components are represented with the open curve.

It is the object of the invention to comprehensively portray the individual repertoire of Ig-mediated binding activities of organisms, especially humans suffering from atopic diseases and/or autoimmune diseases, using recombinant Ig-specific V genes. All classes of immunoglobulins are to be taken into account since, in addition to the IgE-specific reactions, the binding of antibodies from other immunoglobulin classes to the same antigen can be an important regulator for the inflammatory events.

The following definitions are to be applied to the whole of the present application.

Organism: This term includes all life forms which may be affected by disorders of the immune function, such as atopic diseases (allergies) and/or autoimmune diseases. These are, in particular, mammals including humans.

Immunological reaction profile: This term describes the ability of an organism to form specific antibodies against an antigen.

With the present in vitro process for determining the immunological reaction profile of an organism, an individual antigen-specific V gene repertoire can be portrayed in a short time, and the Ig isotype can be specifically differentiated without putting a load on the organism. Thus, it becomes possible to cover and evaluate courses of diseases, mainly those based on disorders of B-cell mediated functions, by means of antigen- and isotype-specific reaction profiles.

The invention relates to a process for determining the immunological reaction profile of an organism, comprising the following steps: (a) isolating once or several times a fraction containing B cells from body fluids and/or tissues; (b) isolating individual B cells or their genetic material and depositing one or more B cells or their genetic material into a reaction vessel; (c) amplification of the genetic material coding the variable regions of an antibody expressed by an isolated B cell; (d) preparation of recombinant antibodies by expressing the cloned amplification products; and (e) determining the binding of the recombinant antibody to recombinant and/or native antigens. This process enables the determination of an immunological reaction profile of organisms, especially humans, whose immune system is not obviously disturbed, especially for determining the potential of a predisposition for atopic diseases or antibody-mediated autoimmune diseases. This process is also suitable for determining the immunological reaction profile of organisms, such as humans, with disorders of the immune function. In particular, the process according to the invention is suitable for determining the immunological reaction profile in disorders of the immune function which include the following diseases: allergies, atopic diseases, antibody-mediated autoimmune diseases, such as antiglomerular basement membrane disease; rheumatoid arthritis; autoimmune diseases of the nervous system, e.g., multiple sclerosis; insulin-dependent diabetes mellitus; systemic lupus erythematosus; pemphigus; Addison's disease; autoimmune hemolytic anemia; antiphospholipid syndrome; Duhring-Brocq syndrome; IgA glomerulonephritis; membranous glomerulonephritis; Goodpasture's syndrome; Graves' disease; Lambert-Eaton myasthenic syndrome; sympathic ophthalmia; bullous pemphigoid; autoimmune polyendokrinopathies; idiopathic thrombocytopenic purpura; Reiter's syndrome; autoimmune thyroiditis; Hashimoto's thyroiditis; primary myxedema; thyrotoxicosis (Basedow's disease); myasthenia gravis; pernicious anemia; autoimmune leukopenia; idiopathic thrombocytopenia; primary biliary cirrhosis; autoimmune hepatitis; colitis ulcerosa; Sjögren's syndrome; rheumatic fever; dermatomyositis; polymyositis; progressive systemic sclerosis; Wegner's granulomatosis; panarteritis nodosa; periarteritis nodosa; and hypersensitivity angitis, etc. In the process according to the invention, the immunological reaction profile is established from the genetic material of the B cells and compared quantitatively and qualitatively with the reaction profile from the serum. In the process according to the invention, the B cell containing fraction of peripheral mononuclear cells is isolated by density centrifugation from blood samples. The isolation of individual B cells preferably comprises the following steps: (a) labeling of the B cells by fluorochrome-coupled antibodies, preferably with antibodies specific for CD19, CD85 and CD138, CD19, CD85, CD138, CD10, CD20, CD21, CD22, CD23, CD24, CD27, CD37, CD38, CD39, CD40, CD72, CD73, CD74, CDw75, CDw76, CD77, CDw78, CD79, CD80, CD81, CD82, CD83, CDw84, CD85 and/or CD86, etc.; (b) the selection of the labeled B cells by flow cytometry; and (c) the depositing of one or more B cells into a reaction vessel. In the process according to the invention, the B cells are immortalized by EBV transformation after the isolation step and the depositing of single cells. It is also possible to fuse the B cells with myeloma cells after the isolation step and the depositing of single cells. The process according to the invention for determining the immunological reaction profile comprises the following amplification steps: (a) cDNA-generating RT reactions; (b) PCR reactions with the cDNA as a template; and (c) nested PCR reactions with the amplification products of the PCR reactions as templates. In such RT reactions, primers whose sequence is complementary to the constant regions of the light and heavy chains are employed to obtain cDNAs as amplification products. In the PCR reactions, the cDNA is employed as the template, and degenerate primers whose sequence is complementary to the variable regions in the framework 1 region of the 6 gene families of the heavy chains are employed, and/or in the PCR reactions, the cDNA is employed as the template, and degenerate primers are employed for the 4 gene families of the κ chains, and/or in the PCR reactions, the cDNA is employed as the template, and degenerate primers are employed for the constant regions of the ε, γ and κ chains. In the "nested" PCR reactions, the amplification products of the PCR reaction are employed as the template, and 5' primers whose sequence is complementary to the first 6 codons of the $V_H$ or $V_L$ regions and 3' primers whose sequence is complementary to the "nested" constant regions of the κ, λ, α1, α2, γ1, γ2, γ3, γ4, μ and ε chains are employed. In the process according to the invention, the amplification products from the reaction mixtures which contain amplificates of the $V_L$ and $V_H$ regions are cloned into a vector, and recombinant antibodies are obtained by expressing the vectors in bacterial and/or eukaryotic expression systems. The vectors of the process according to the invention which contain the amplification products are also claimed. Also, the use of the amplification products according to the invention for the preparation of expression vectors is claimed. Further, the use of the vectors for the preparation of recombinant antibodies as well as the thus obtainable recombinant antibodies are claimed. The process according to the invention also comprises the determination of the binding of the recombinant antibodies to antigens by automated methods, especially by solid-phase coupled binding assays, flow cytometry, resonance spectrometry and/or chip arrays with recombinant and native antigens in a native or denatured form. The use of the recombinant antibodies for determining their binding activities for recombinant antigens is also claimed.

Starting from peripheral blood samples, the present invention for determining the immunological reaction profile of an organism comprises the following steps: (a) isolating once or several times B cells and sorting them and depositing of single cells and the immortalization of the B cells by EBV transformation or heteromyeloma fusion of the B cells with the B lymphoma cell line KGH6/B5; (b) isolating the genetic material of said one or more B cells; (c) specific amplification of the variable regions of light κ and λ chains, and of the variable regions of the heavy Igα1, Igα2, Igγ1, Igγ2a, Igγ2b, Igγ3, Igγ4, Igμ and Igε chains by means of different PCR reactions including a single cell "nested" RT-PCR; (d) the functional expression of the amplificates in a bacterial expression system for the recombinant preparation of antibodies; and (e) the automated qualitative and quantitative analysis of the binding activities of recombinant antigens by solid-phase coupled binding assays, flow cytometry, resonance spectrometry, chip arrays with recombinant and native antigens in a native or recombinant form to thus be able to also cover non-proteinogenic epitope structures originating from post-translational modifications.

DETAILED DESCRIPTION

The present invention relates to a process for determining the immunological reaction profile of an organism which comprises several steps. At first, the allergen-specific plasma and memory B cells are enriched from a body fluid and/or tissues which contain B cells. The enriching of these cells can be effected, for example, by the density centrifugation of peripheral mononuclear cells from blood samples. Dead cell populations are excreted by means of propidium iodide. The allergen-specific memory cell population is 1.2% on average in the FACS analysis. As described in the Methods section, the memory B cell population is sorted as single cells. The isolation comprises three steps, namely (a) the labeling of the B cells by fluorochrome-coupled antibodies, wherein antibodies specific for CD19, CD138, CD10, CD20, CD21, CD22, CD23, CD24, CD27, CD37, CD38, CD39, CD40, CD72, CD73, CD74, CDw75, CDw76, CD77, CDw78, CD79, CD80, CD81, CD82, CD83, CDw84, CD85 and/or CD86 etc. may be used; (b) the selection of the labeled B cells by flow cytometry; and (c) the depositing of one or more cells into a reaction vessel. The deposited cells can be immortalized by transformation with the Epstein Barr virus (EBV); it is also possible to fuse the isolated/deposited/sorted B cells with myeloma cells. The RNA isolation from the sorted cells follows as a second step. As a third step, the amplification of the genetic material coding the variable regions of the antibody expressed by the B cell is effected. First, an RT-PCR is performed for the amplification of immunoglobulin heavy and light chains. For obtaining the cDNA amplification products, primers whose sequence is complementary to the constant regions of the light and heavy chains are employed. In particular, the following primers are employed for the RT reactions: (a) light chain κ: 5' AAC AGA GGC AGT TCC AGA (SEQ ID NO:1); (b) light chain λ: 5' TGTGGC CTT GTT GGC TTG (SEQ ID NO:2); (c) heavy chain α: 5' CTTGCA GAC ACT TGG TGT TCG TGC (SEQ ID NO:3); (d) heavy chains γ1 and γ3: 5' AGG GYG CCA GGG GGA A (SEQ ID NO:4); (e) heavy chain γ2: 5' TTT ACC CRG AGA CAG GGA GAG GC (SEQ ID NO:5); (f) heavy chain γ4: 5' TTT ACC CRG AGA CAG GGA GAG GC (SEQ ID NO:6); (g) heavy chain μ: 5' GCA GGA GAC GAG GGG GA (SEQ ID NO:7); and (h) heavy chain ε: 5' TTT ACC GGG ATT TAC AGA CAC (SEQ ID NO:8). The heavy chains are isolated for all isotypes. To date, it has been possible to amplify and express allergen-specific variants of various isotypes. According to nature, however, the Ig class gamma 1 is found most frequently. It is noted that the same variable genes are not automatically used for all isotypes (see [14]). Rather, an isotype-specific use of V gene classes is found in this case too. The cDNA fragments obtained by the RT-PCR are employed as templates in PCR reactions which contain degenerate primers whose sequence is complementary to the variable regions in the framework 1 region of the 6 gene families of the heavy chains, and/or whose sequence is complementary to the 4 gene families of the κ chains, and/or whose sequence is complementary to the 3 gene families of the λ chains, and/or with degenerate primers for the constant regions of the ε, γ and κ chains. In particular, the following "sense" primers are employed for the variable region of the light κ chains: hVkI Back 5' GAC MTC VWG HTS ACC CAG TCT CC (SEQ ID NO:9); hVkII Back 5' GAC CTC CAG HTG ACC CAR WSY CC (SEQ ID NO:10); hVkIII Back 5' GAC CTC CAR HTS ASK CAG TCT CC (SEQ ID NO:11); hVkIV Back 5' GAK VTY GTG ATG ACY CAG WCT CC (SEQ ID NO:12); hVkV Back 5' GAC ATC SWG ATG ACC MAG TCT CC (SEQ ID NO:13); hVkVI Back 5' GAC CTC GTG HTG ACB CAG DSY CC (SEQ ID NO:14); hVkVII Back 5' GAC ATS VWG CTC ACS CAG TCT CC (SEQ ID NO:15). As "antisense" primers, the following primers are employed for the variable region of the light chains: hVkI For 5' TCG TTT GAT CTC CAS YYK KGT CC (SEQ ID NO:16); hVkII For 5' TCG TTT RAT YAG TAC CYK KGT CC (SEQ ID NO:17); hVkIII For 5' TCG TTT GAY HTS CAS CTT KGT CC (SEQ ID NO:18). For the variable regions of the light λ chain, the following "sense" primers are employed: hVkI Back 5' CAG TCT SWG CTG ACK CAG CCR CC (SEQ ID NO:19); hVλII Back 5' CAG TCT SMG CTG ACT CAG CCW SS (SEQ ID NO:20); hVλIII Back 5' CAS GYT WTA YTG ACT CAA YCG CC (SEQ ID NO:21); hVλIV Back 5' TCC TMT GWG CTG ACW CAR CCA CC (SEQ ID NO:22); hVλV Back 5' TCK TMT GAR CTG ACT CAR GAC CC (SEQ ID NO:23); hVλVI Back 5' CAG TCT GTG CTG ACT CAG SMD SS (SEQ ID NO:24). As "antisense" primers for the variable regions of the λ chain, there are employed: hVλI For 5' ACCKAG RAC GGT SAS CTB GGT CC (SEQ ID NO:25); hVλII For 5' ACY TAR GAC GGT SAV YTT GGT CC (SEQ ID NO:26); hVλIII For 5' ACC TAR RAC GGT SAV CTK GGT CC, (SEQ ID NO:27). Further, the following primers were employed as immunoglobulin-specific primers ("sense") for the heavy chains: hVHI 5' CAG GTG CAG CTG SWG SAR TCK GG (SEQ ID NO:28); hVHII sense 5' CAG STG CAK CTG CAG GAG TCS GG (SEQ ID NO:29); HvhIII sense 5' CAG GTG SAG CTG SWG SAG TCH GG (SEQ ID NO:30); HvhIV sense 5' GAG GTG CAG CTR CAK SAG TSG GG (SEQ ID NO:31); HvhV sense 5' GAG GTG CAR CTG KTG SAG TCN GS (SEQ ID NO:32); HvhVI sense 5' GAG GTG CGR CTG GTG SAG WSK GG (SEQ ID NO:33); HvhVII sense 5' CAG GTS AAS YTA AGG GAG TCT GG (SEQ ID NO:34). As "antisense" immunoglobulin-specific primers for the heavy chains, there were employed: IgA1 5' GAA GAC CTT GGG GCT GGT CGG GGA TG (SEQ ID NO:35); IgA2 5' ATG CGA CGA CCA CGT TCC CAT CTT G (SEQ ID NO:36); IgE 5' GTT CTG GAT CAG GCA GGC GAG GGT GC (SEQ ID NO:37); IgG1 5' CTC GAT GGGGGC TGG GAG GGC TTT G (SEQ ID NO:38); IgG2 5' CCT GGT GCA CAA CGG TGA GGA CG (SEQ ID NO:39); IgG3 5' GTC CGG GAA ATC ATA AGG GTA TC (SEQ ID NO:40); IgG4 5' GAG GAC GGG AGG CCT TTG YTG GAG (SEQ ID NO:41); IgM 5' CAG GAG ACG AGG GGG AAA AG (SEQ ID NO:42). The class-specific differentiation is achieved by a reamplification of the heavy chains in a "nested" PCR, in which amplification products are again obtained. In the "nested" PCR reactions, the amplification products from the PCR reaction are employed as the template, and 5' primers whose sequence is complementary to the first 6 codons of the $V_H$ region or $V_L$ regions and 3' primers whose sequence is complementary to the "nested" constant regions of the κ, λ, α1, α2, γ1, γ2, γ3, γ4, μ and ε chains are employed to obtain an amplification product. The "sense" primers of the PCR reaction are used as the "sense" primers. The following immunoglobulin class-specific oligonucleotides are employed as "antisense" primers: IgA1 5' GAAAAC CCA AGC GCT CAG CCC AAA CTC CAT (SEQ ID NO:43); IgA2 5' CCT TGG CGG GGC TGG TCG GGG ATG (SEQ ID NO:44); IgE 5' CAG GAC GAC TGT AAG ATC TTC ACG (SEQ ID NO:45); IgG1 5' CCC CAG AGG TGC TCT TGG AGG AGG GT (SEQ ID NO:46); IgG2 5' CCG CTG TGC TCT CAG AGG TGC TCC TG (SEQ ID NO:47); IgG3 5' GGC CGC TGT GCC CCC AGA GGT GCT C (SEQ ID NO:48); IgG4 5' GCA GCC CAG GGC GGC TGT GCT CTC G (SEQ ID NO:49); IgM 5' GAA AAG GGT TGG GGC GGA TGC (SEQ ID NO:50). The amplification reactions are performed with Taq polymerase, and the obtained fragments which contain $V_L$ and $V_H$ regions are cloned into vectors. In particular, the TA cloning system is employed. The fourth step of the process for determining the immunological reaction profile of an organism is the recombinant production of antibodies by expressing the amplificates. Thus, the fragments cloned into vectors are expressed in bacterial and/or eukaryotic expression systems. The vectors are used for the preparation of recombinant antibodies. In particular, the resulting immunoglobulin fragments are expressed first in phages as "single-chain antibodies" or as "Fab fragments". The thus obtained antibodies are used for analyzing their binding activity towards allergens. The binding affinity of the "single-chain antibodies" is analyzed by means of "biosensor chip" technology. For the expression of the Fab fragments as soluble proteins, the expression system described under Example 1 is used.

For measuring the binding affinity, recombinant Betv1 as an antigen was covalently coupled to a CM5 sensor chip. Further, two sequenced heavy and light chains as well as a heavy chain alone were cloned into a suitable phage expression system. Subsequently, two Fab-expressing phages were injected. The experiment shows two Fab fragments of different affinities (Fab high, fab low). The specificity is ensured by the two controls (F-heavy and vector). The experiment shows clearly that affine antigen-specific B cells can be isolated with the method described.

Thus, the process is suitable for determining the potential for atopic diseases or antibody-mediated autoimmune diseases, as well as for determining the immunological reaction profile of subjects who already exhibit obvious immune function disorders. The immune function disorders which can be analyzed by means of the present invention include the following diseases: antiglomerular basement membrane disease; rheumatoid arthritis; autoimmune diseases of the nervous system, e.g., multiple sclerosis; insulin-dependent diabetes mellitus; systemic lupus erythematosus; pemphigus; Addison's disease; autoimmune hemolytic anemia; antiphospholipid syndrome; Duhring-Brocq syndrome; IgA glomerulonephritis; membranous glomerulonephritis; Goodpasture's syndrome; Graves' disease; Lambert-Eaton myasthenic syndrome; sympathic ophthalmia; bullous pemphigoid; autoimmune polyendokrinopathies; idiopathic thrombocytopenic purpura; Reiter's syndrome; autoimmune thyroiditis; Hashimoto's thyroiditis; primary myxedema; thyrotoxicosis (Basedow's disease); myasthenia gravis; pernicious anemia; autoimmune leukopenia; idiopathic thrombocytopenia; primary biliary cirrhosis; autoimmune hepatitis; colitis ulcerosa; Sjögren's syndrome; rheumatic fever; dermatomyositis; polymyositis; progressive systemic sclerosis; Wegner's granulomatosis; panarteritis nodosa; Periarteritis nodosa; and hypersensitivity angitis, etc. The process allows to compare the genetically established reaction profile with reaction profiles from the serum qualitatively and quantitatively. In the following, results which relate to the experiments described in the Examples are discussed.

Isolation of Antigen-Specific B Cells

The starting point for the selection steps is leukocyte preparations from Ficoll gradient centrifugations based on buffy coats or peripheral whole blood. The proportion of CD19$^+$ cells was 10.6±0.6% at a total cell number of 3.4±0.7×10$^7$ PBMCs.

The separation of antigen-specific B cells was performed by means of MACS methods (Miltenyi). In a double selection process, CD19$^+$ cells were first isolated, and from this fraction, antigen-specifically labeled cells were isolated. Their proportion varied between 0.01 and 0.05%. The cells were subsequently subjected to EBV transformation.

Figure 2:
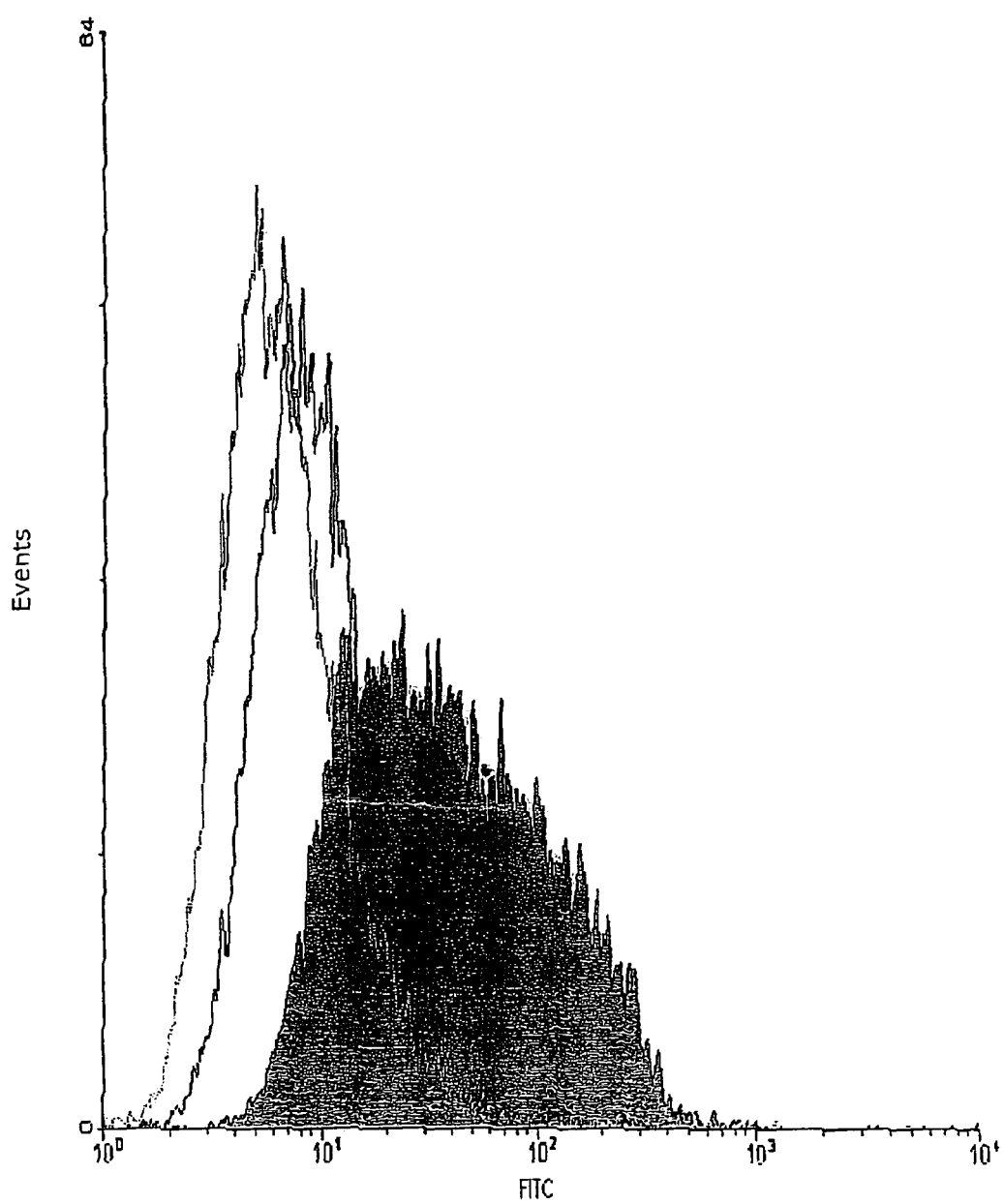
FIG. 2: With a FACS analysis, the illustration shows a comparison between the binding activities of the Phl-p5b-specific EBV-transformed cell line (solid curve) with an EBV-transformed cell line with no relation to Phl p5b (open curve). Non-specific reactions which occur as a background of the measurements by using secondary detection components are represented with the open curve.

The binding properties of the cultured antigen-specifically selected B cells were analyzed by flow cytometry. A recombinant fusion protein (PV 21/2 Ang II) served as the antigen; it consisted of the actual antigen PV 21/2, a fragment of the timothy grass allergen rPhl pVb, coupled to human angiogenin (Ang II). The fusion protein LPV-ETA', a fusion of the full-length allergen with the toxin domain ETA', was employed as a further antigen. In order to be able to distinguish non-antigen-specific reactions, in terms of the previous selection against the allergen, from reactions which are directed against epitopes of the toxin domains, experiments with recombinant protein fusions were performed in which the allergen domain had been exchanged for recombinant scFv specific for the surface antigens GD2 (NAng GDII) or the epidermal growth factor receptor (HAI ETA'). In contrast to PV 21/2 Ang II and LPV-ETA', the use of both control antigens in the FACS analysis showed fluorescence intensities which corresponded to the background level of the secondary detection components (FIG. 1 and FIG. 2). A further experimental approach was intended to clarify whether the proteins employed generally bind B cells or can be attributed to properties of specific B cells. Thus, the same experimental approach was performed before the background of a great B cell receptor repertoire with freshly prepared PBMCs, and the binding activity of the CD19+ fraction was examined (FIG. 1). Identical fluorescence signal recognitions are obtained for all allergen and control variants, and thus, no indications of non-specific binding by B cells are observed.

For the selection of antigen-specific B cells by flow cytometry, 4×10$^6$ EBV-transformed cells were employed. The cells were originally derived from a MACS selection as an antigen-specific cell line. As the age of the culture increased, the proportion of non-binding cells grew, presumably genetically unstable clones which could not express any functional immunoglobulins or B cell receptors. The remaining antigen-specific cells could be distinguished clearly from non-specific ones in the flow cytometer and could be isolated through a corresponding selection gate. From the original population, 3×10$^5$ cells with a purity of 97% was isolated and cultured in densities of 1,000 cells per cavity. After 2 weeks, the antigen-specific binding properties were tested (FIG. 2). The antigen (LPV) was present as a fusion protein coupled to the toxin component (ETA'). In order to be able to detect reactions against the toxin domain, control experiments were performed by means of a fusion construct (HAI-ETA') in which the antigen domain had been replaced by recombinant EGF (epidermal growth factor). The bindings were exclusively directed against the antigen domain (LPV). The fluorescence intensity of the control antigen was the same as that of the background (secondary and tertiary detection components).

In order to check whether the interactions between the antigen and B cells represent properties of specific clones in terms of an antibody/antigen reaction, antigen-specifically selected B cells were compared with unselected cell lines. The unselected cells represent a clonal B cell repertoire from a buffy coat, which were immortalized by EBV transformation and cultured. The experimental approach corresponds to that described above, except for the control antigen. As compared to unselected B cells, 4.1 times higher binding activities (mean fluorescence intensity) were established for the antigen-specifically selected cells.

Immortalization by EBV Transformation

Figure 3A:
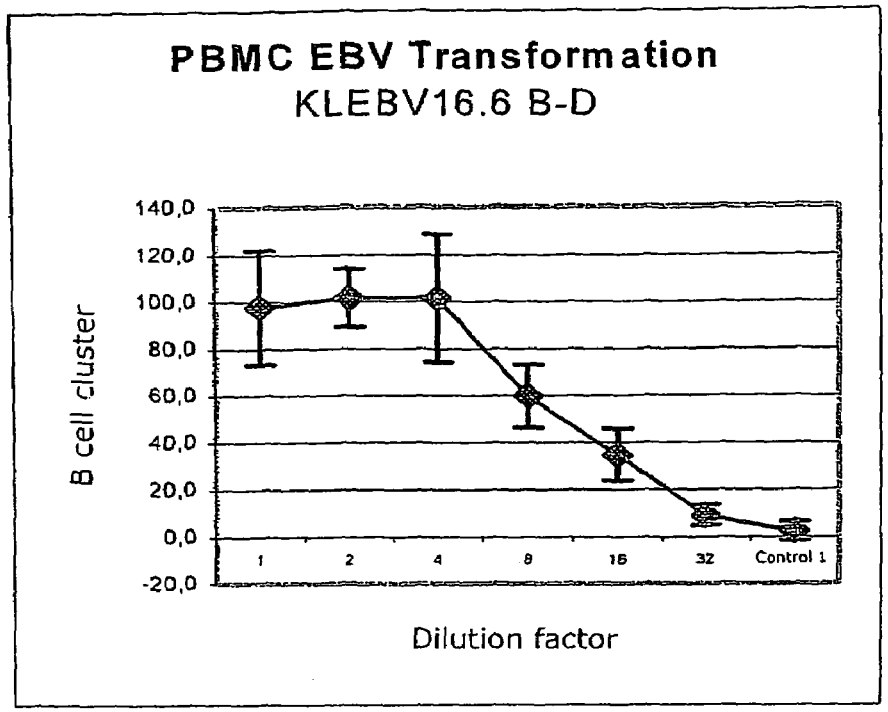
FIG. 3: (a) and (b) show the number of B cell clusters upon EBV transformation as a function of the serial dilutions of the EBV supernatants. Calculated correlation coefficients: (a)=−0.95; (b)=−0.96, n=3.
Figure 3B:
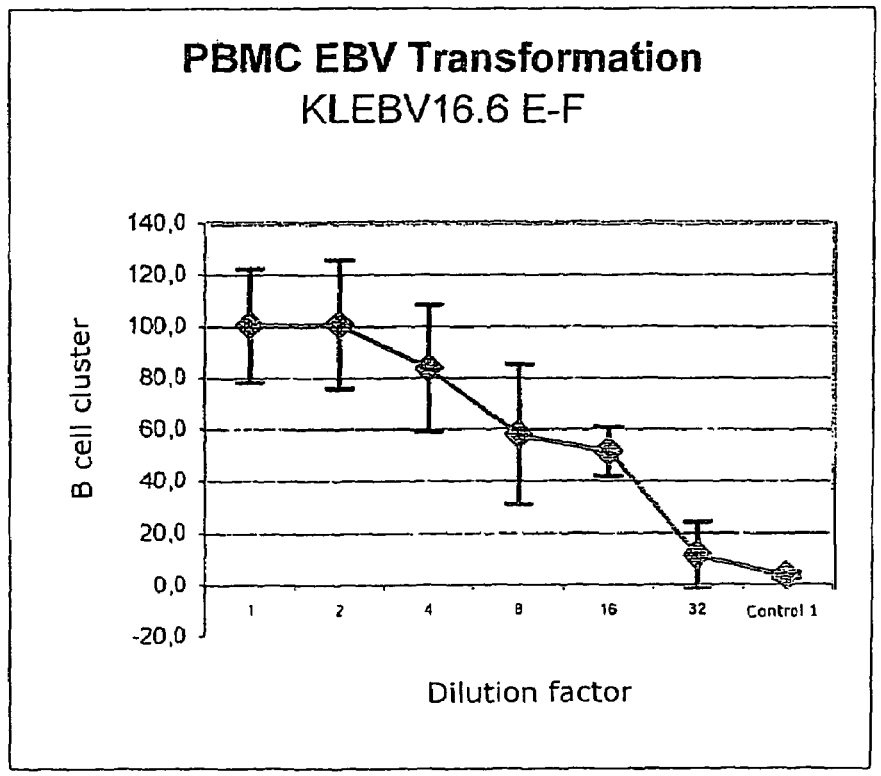

For immortalizing primary B cells, leukocyte preparations were subjected to the process as described under Example 1.2. To determine the optimum transformation parameters, the transformation frequency of EBV-containing supernatants was established with unselected PBMCs. For a constant number of cells (1×10$^5$), transformations were performed with continuous two-times dilutions of the EBV-containing supernatant with two different PBMC preparations. After 17 days of culturing phase, transformed B cells could be observed as cell aggregates growing in the form of clusters. For simplification, each cluster was counted as a single clone. The number of clusters was related to the number of starting cells and to the respective dilution level of the EBV-containing supernatants (FIG. 3). The transformation frequencies were 3.1×10$^{-3}$±1.7×10$^{-3}$ for PBMC preparation A and 3.5×10$^{-3}$±2.4×10$^{-3}$ for preparation B.

Figure 4:
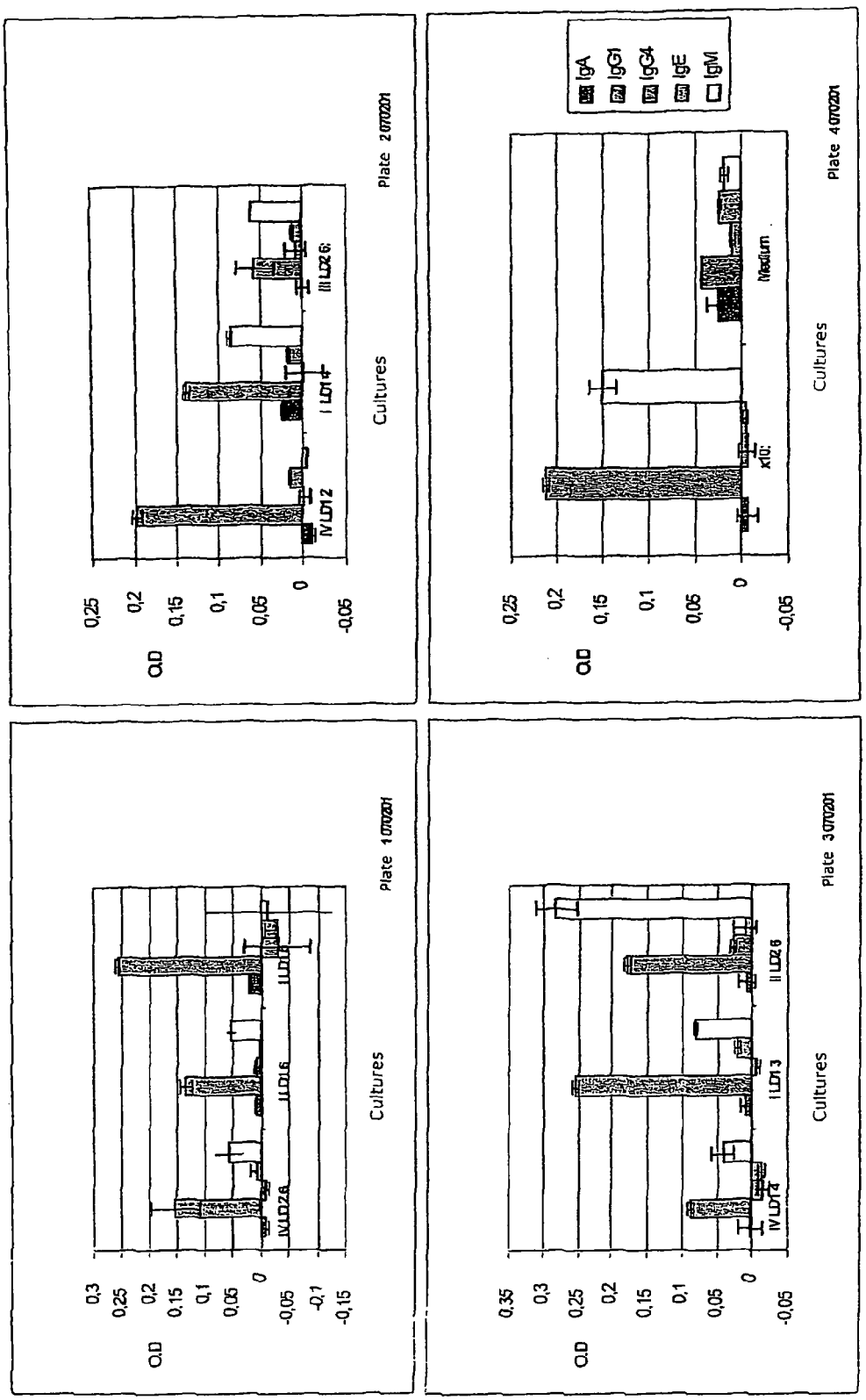
FIG. 4: Immune class specific ELISA with supernatants of EBV-transformed B cells. The assay was performed for 10 subcultures. The values are based on control-corrected duplicate determinations with mixtures with no primary detection component. A mixture against culture medium served as a negative control.
Figure 5:
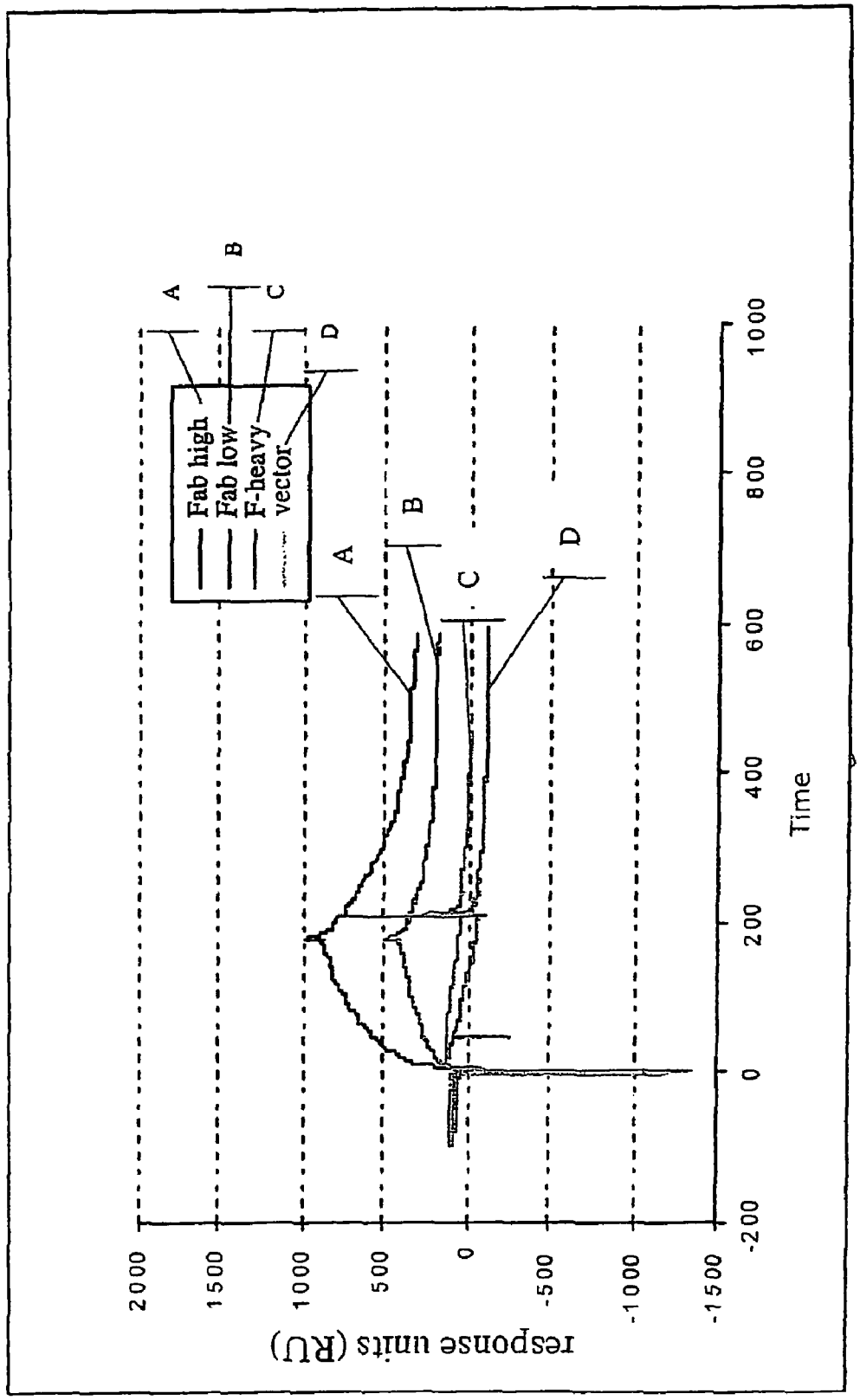
FIG. 5: Affinity measurement or recloned and expressed anti-Betvl-specific Fab fragments by means of the BIACORE method.

In order to clarify which immunoglobulin classes the selection cultures under permanent culture secrete, culture supernatants were tested by solid phase ELISA. The examination comprised human antibodies of classes IgA, IgE, IgG1, IgG4 and IgM. In all cultures tested, secreted antibodies could be detected, which were to be attributed exclusively to classes IgG1 and IgM (FIG. 4).

Lymphocyte Isolation by Means of Ficoll Density Gradient Centrifugation

The separation of antigen-specific B cells was preceded by a leukocyte preparation by means of Ficoll gradient centrifugation (see also Example 1). The starting material for the preparation is peripheral whole blood from patients. From allergy sufferers, 10 ml of whole blood is withdrawn into heparin-coated blood collection tubes. This is followed by a density gradient centrifugation. The supernatant contains the serum diluted at about 1:3 and can be stored at −20° C. for ELISA. The solid blood components (erythrocytes, platelets etc.) sink to the ground of the sample tube, and the lymphocytes appear as a ring between the serum and Ficoll solution and are removed with a pipette. The lymphocytes are washed in a volume of 30 ml of FACS buffer (1×PBS, 0.5% BSA, 4 mM EDTA) at 4° C. for 20 min at 1500 rpm with brake, and the lymphocyte pellet is resuspended in 1 ml of FACS buffer.

Isolation of B Cells by Means of CD19 MACS Enrichment

The lymphocytes are incubated with an anti-human CD19 MACS antibody (Miltenyi) (see also Example 1). After two washes, up to 2×10$^8$ total cells are charged on the MS-MACS separation column (Miltenyi). Previously, the column is equilibrated with 500 µl of FACS buffer, followed by three washes with 500 µl of FACS buffer. The column is then removed from the magnet, covered with a layer of 1 ml of FACS buffer, and the enriched cells are carefully pushed through with the syringe piston. The purity can be increased to 99% if the positive, CD19$^+$-enriched fraction is passed over a second equilibrated column.

Isolation of Antigen-Specific Memory Cells

High affinity antibodies are formed by antigen-specific B cells in germinal centers of secondary lymphatic organs by means of somatic mutation upon antigen contact. This is why the further enrichment of CD19$^+$ populations is focused on the isolation of memory cells. For the enrichment of memory cells, standard published anti-CD antibodies (surface markers) are used. The specificity of the B cell population for the antigen is achieved by providing the antigen with a fluorescence marker (e.g., FITC). After staining, the fluorescence of the cells is established in a FACSVantage flow cytometer. Cells whose signals exceed the maximum fluorescence intensity of the control by one power of ten are detected by a selection gate and deposited in a 96 well plate format by the single cell sorting mode.

RNA Isolation, cDNA Synthesis and RT-PCR of Birch Pollen Reactive Immunoglobulin Heavy and Light Chains The positive cells were immediately sorted into a 96 well plate in which 20 µl of 1×RT-PCR buffer (QIAGEN oneStep RT-PCR Kit) had been charged. The RNA isolation is performed according to the Qiagen standard protocol. For reverse transcription (RT), antisense-specific primers from the 3' region of the constant region of the κ and λ light chains as well as of the isotype-specific heavy chain (ε, α, µ and γ subclasses) were used (the sequences are completely present in the sequence data base). This is followed by a PCR amplification step in which an aliquot of the RT mixture with the respective sense primers from the 5' variable region of the κ and λ light chains as well as the variable heavy chain is added. Standard published V gene mixes of heavy and light chains are used as primers. The PCR conditions were optimized for the following times and temperatures (45 s at 95° C., 45 s at 72° C., 1 min at 59° C.; 35 repeats). To increase the specificity of the PCR, a semi-nested PCR protocol can be employed. The resulting PCR products are sequenced directly (ABI). The PCR product is recloned into suitable expression vectors as judged by the obtained sequence.

Expression of Recombinant Birch Pollen Reactive Immunoglobulin Heavy and Light Chains The expression of the heavy and light chains as scFv or Fab fragments is effected as described in Example 1.

Immortalization of Antigen-Specific B Lymphocytes by Means of EBV Transformation The immortalization is achieved by means of EBV transformation. The method is explained in some detail in Example 1.

EXAMPLES

1. Isolation of Timothy Grass Pollen Reactive Recombinant Antibodies and Fusions 1.1. Isolation of Antigen-Specific B Cells The separation of antigen-specific B cells was performed by means of MACS methods (FIG. 1). Biotin-conjugated timothy grass pollen allergen (rPhl pVb) served as the antigen. The labeling of immortalized cells was effected with 2 µg of antigen/$10^6$ cells, a washing step and subsequent incubation with streptavidin-coupled paramagnetic microbeads. The labeled lymphocytes were separated from non-labeled cells by retention in the magnetic field and subjected to culture.

Alternatively to MACS isolation, specific B cells were selected by means of flow cytometry against Phl pVb (FACSVantage SE, Becton Dickinson). For labeling specific cells, a fusion of the recombinant allergen Phl pVb with the toxin domain of the Pseudomonas exotoxin A (ETA), LPV-ETA, was employed (2 µg of LPV-ETA' per 1×$10^6$ cells in 300 µl, 30 min/4° C.). The fusion protein can be detected by a polyhistidine tag. Monoclonal anti-His antibodies (working concentration 1:2000) and goat anti-mouse FITC conjugate (1:1000) served as detection antibodies. After staining, the fluorescence of the cells was established in a FACSVantage SE flow cytometer in FL 1/FL 2. Cells whose signals exceeded the maximum fluorescence intensity of the control by one power of ten were detected by a selection gate and deposited in a 96 well plate format by the single cell sorting mode. The selected cells were subjected to permanent culture and tested for specific binding activity.

1.2. Immortalization by EBV Transformation

For obtaining EBV-containing supernatants, cryopreserved B-95-8 cells (CATCC CLR 1612) were cultured (37° C., 5% $CO_2$) at a concentration of 1×$10^6$ cells in 10 ml of medium (RPMI 1640, 10% FCS, 50 µg/ml streptomycin, 50 U/ml penicillin, 2 mM L-glutamine). After the addition of 5 ml of culture medium on the following day and another 10 days of culturing without adding medium, the cell culture supernatants were filtered through a 0.2 µm filter, aliquoted and frozen at −196° C.

For transformation, peripheral mononuclear cells (PBMCs) obtained by density gradient centrifugation from whole blood or buffy coats and subsequently subjected to the selection process as described under 1.1 were employed. The transformation mixes each consisted of 100 µl of cell suspension ($10^5$ cells), 10 µl of cyclosporin A (2.6 µg/ml final) and 100 µl of EBV supernatant. After 17 days of culturing (37° C., 5% $CO_2$) without changing the medium, immortalized B cells could be observed by the cell aggregates formed, and subjected to culture. The cell culture supernatant was examined for secreted immunoglobulins by means of ELISA (FIG. 3). The detection was effected by means of specific antibodies against human immunoglobulin classes (IgA, IgG1, IgG4, IgE and IgM) as well as biotin-conjugated anti-goat or anti-mouse antibodies and alkaline phosphatase-coupled streptavidin. The culture medium (RPMI 1640, 10% FCS) and one mix each without a primary detection component were employed as negative controls. The examined supernatants were derived from four months old cultures after the previous subculturing of immunoglobulin secreting cells by "limiting dilution" (125 cells/cavity).

1.3. Expression of Recombinant V Gene Fragments Capable of Binding

Single-strand variable fragments (scFv) capable of binding were cloned by means of standard methods [6] into a derivative of the phagemide pCANTAB or the bacterial expression vector pBM1.1 (7) and thereby fused with a deletion mutant of the Pseudomonas exotoxin A. The ligation mixtures were subjected to phenol extraction and ethanol precipitation and resuspended in 10 µl of $H_2O$. After a described protocol [7], 2.5 µl of this DNA solution was introduced into E. coli BL21 (DE3) by electroporation. Transformed bacteria were cultured on kanamycin-containing medium (2×LB with 50 µg of kanamycin/ml and 2% glucose). Positive clones were verified by restriction analysis.

The processes for cloning and expression of the scFv have already been described under:

| ScFv | Target antigen | Disease | References |
| --- | --- | --- | --- |
| Ki-4 | CD30 receptor | Hodgkin's lymphoma | [8, 9] |
| Ki-3 | CD30 receptor | Hodgkin's lymphoma | [10, 11] |
| hHAK30 | CD30 receptor | Hodgkin's lymphoma | [12] |
| RFT5 | CD25 receptor | Hodgkin's lymphoma | [13-15] |
| 14.18 | GD2 antigen | neuroblastoma | [13, 14] |

1.4 Growth and Induction of the Genetically Engineered Organisms

Transformed E. coli BL21 (DE3) were incubated in Terrific Broth [TB] medium [6] (1.2% Bacto-Trypton, 2.4% Bacto-Yeast Extract, 0.4% 0.17 M $KH_2PO_4$, 0.72 M $K_2HPO_4$) supplemented with 50 µg/ml kanamycin and 0.5 mM $ZnCl_2$ for 12-15 hours or over night at 26° C. and 200 rpm. Subsequently, the cultures were transferred into 0.5 l Erlenmeyer flasks with baffles in a volume of 200 ml of TB medium and grown to an $OD_{600}$ of 2. Subsequently, the osmotic value of the medium was increased with 0.5 M sorbitol, 4% NaCl, and 10 mM betaine or ectoine was added as a compatible solute. Both substances have comparable effects; however, ectoine can also be synthesized directly by the cells through cotransformation with plasmids of the pOSM series or by additional coding on the pBM1.1 derivative.

The cultures were incubated at 26° C./200 rpm for 15-60 min, followed by initiating the expression of the target protein by adding 2 mM IPTG. After an $OD_{600}$ of 2.3-2.4 was reached, the bacteria were harvested by a centrifugation step (3,700 g, 10 min, 4° C.). All further steps were performed on ice. After a washing step (the pellet was resuspended in 75 mM Tris/HCl, pH 8, 4% NaCl, 10% glycerol and homogenized) followed by centrifugation (3,700 g, 10 min, 4° C.), the weight of the wet pellet was determined, and before the lysis, the bacterial pellet was shock frozen for 10 min at –80° C. or –196° C.

An alternative approach for the expression of recombinant scFv is performed by the following method: Transformed *E. coli* TG1 are picked and taken up in 2×TY, 100 μg/ml ampicillin, 2% glucose, and incubated over night at 37° C. with shaking. Subsequently, the culture incubated over night is diluted 1:100 in 50 ml of 2×YT broth medium, 100 mg/ml ampicillin, 2% glucose, and grown at 37° C. with shaking to a density of 0.9 $OD_{600\ nm}$. The mixture is centrifuged for 10 minutes at 4,000 rpm, and the pellet is resuspended in 10 ml 2×TY, 100 μg/ml ampicillin, 1 mM ITPG. Under continuous shaking at 30° C., the mixture is incubated for at least another 5 hours.

After 5 hours of induction, the construct can be harvested from the periplasma. Thus, the culture is cooled on ice for 10 to 20 minutes, followed by centrifuging in a microfuge at 6,000 rpm for 5 minutes. The pellets were taken up in 10% of the original volume in PBS, 1 M NaCl, 1 mM EDTA, 4° C., and then incubated on ice for 30 minutes. This is followed by another centrifugation step in a microfuge for 10 minutes at 6,000 rpm to remove the cells. The supernatant is transferred into a fresh tube and centrifuged at 14,000 rpm, 4° C., for 10 minutes to sediment debris. The periplasmic protein fraction is found in the supernatant.

1.5. Lysis and Purification of Recombinant scFvs and scFv Fusions

After the freezing phase, the bacterial pellet was resuspended in ultrasonic buffer (75 mM Tris/HCl, pH 8, 300 mM NaCl, 1 tablet of protease inhibitors [Boehringer]/50 ml, 5 mM DTT, 10 mM EDTA, 10% glycerol) on ice, homogenized (15 min) and then subjected to ultrasonic treatment six times for 30 s at 200 Watt. Between the individual incubation phases, an equally long cooling phase on ice was performed (30 s). In order to obtain the scFv fusions (immunotoxins) quantitatively, it was necessary to refreeze the pellet at –80° C. or –196° C. and to repeat the operations described just above for a maximum of three times. The fractions obtained were combined and subjected to sterile filtration. After sequential precipitation in 50% ammonium sulfate (AS), the samples were incubated in 30% AS for 4-6 hours, then enriched in 50% AS and finally precipitated over night at 4° C. For recovering the samples, they are centrifuged at 25,000 g for 45 min. The protein pellet was taken up in sample buffer (75 mM Tris/HCl, pH 8, 300 mM NaCl, 10% glycerol). Thereafter, the samples were rebuffered at 4° C. by means of a Hitrap Desalting Column on an FPLC system (75 mM Tris/HCl, pH 8, 300 mM NaCl, 10% glycerol). Subsequent to the desalting column, the protein was charged in a first step for metal chelate chromatography on an Ni-NTA column (Qiagen).

2. Isolation, Characterization and Expression of Birch Pollen Specific Antibodies from Allergy Sufferers 2.1. Isolation of Lymphocytes by Means of Ficoll Density Gradient Centrifugation The separation of antigen-specific B cells is preceded by leukocyte preparation by means of Ficoll gradient centrifugation (see also Example 1). The starting material for the preparation is peripheral whole blood from patients. From allergy sufferers, 10 ml of peripheral whole blood is withdrawn into heparin-coated blood collection tubes. This is followed by a density gradient centrifugation. The supernatant contains the serum diluted at about 1:3 and can be stored at –20° C. for ELISA. The solid blood components (erythrocytes, platelets etc.) sink to the ground of the sample tube, and the lymphocytes appear as a ring between the serum and Ficoll solution and are removed with a pipette. The lymphocytes are washed in a volume of 30 ml of FACS buffer (1×PBS, 0.5% BSA, 4 mM EDTA) at 4° C. for 20 min at 1500 rpm with brake, and the lymphocyte pellet is resuspended in 1 ml of FACS buffer.

2.2. Isolation of B Cells by Means of CD19 MACS Enrichment

The lymphocytes are incubated with an anti-human CD19 MACS antibody (Miltenyi) (see also Example 1). After two washes, up to $2 \times 10^8$ total cells are charged on the MS-MACS separation column (Miltenyi). Previously, the column is equilibrated with 500 μl of FACS buffer, followed by three washes with 500 μl of FACS buffer. The column is then removed from the magnet, covered with a layer of 1 ml of FACS buffer, and the enriched cells are carefully pushed through with the syringe piston. The purity can be increased to 99% if the positive, $CD19^+$-enriched fraction is passed over a second equilibrated column.

2.3. Isolation of Antigen-Specific Memory Cells

High affinity antibodies are formed by antigen-specific B cells in germinal centers of secondary lymphatic organs by means of somatic mutation upon antigen contact. This is why the further enrichment of $CD19^+$ populations is focused on the isolation of memory cells. For the enrichment of memory cells, standard published anti-CD antibodies (surface markers) are used. The specificity of the B cell population for the antigen is achieved by providing the antigen with a fluorescence marker (e.g., FITC). After staining, the fluorescence of the cells is established in a FACSVantage flow cytometer. Cells whose signals exceed the maximum fluorescence intensity of the control by one power of ten are detected by a selection gate and deposited in a 96 well plate format by the single cell sorting mode.

2.4 RNA Isolation, cDNA Synthesis and RT-PCR of Birch Pollen Reactive Immunoglobulin Heavy and Light Chains The positive cells were immediately sorted into a 96 well plate in which 20 μl of 1×RT-PCR buffer (QIAGEN oneStep RT-PCR Kit) had been charged. The RNA isolation is performed according to the Qiagen standard protocol. For reverse transcription (RT), antisense-specific primers from the 3' region of the constant region of the κ and λ light chains as well as of the isotype-specific heavy chain (ε, α, μ and γ subclasses) were used (the sequences are completely present in the sequence data base). This is followed by a PCR amplification step in which an aliquot of the RT mixture with the respective sense primers from the 5' variable region of the κ and λ light chains as well as the variable heavy chain is added. Standard published V gene mixes of heavy and light chains are used as primers. The PCR conditions were optimized for the following times and temperatures (45 s at 95° C., 45 s at 72° C., 1 min at 59° C.; 35 repeats). To increase the specificity of the PCR, a semi-nested PCR protocol can be employed. The resulting PCR products are sequenced directly (ABI). The PCR product is recloned into suitable expression vectors as judged by the obtained sequence.

2.5. Expression of Recombinant Birch Pollen Reactive Immunoglobulin Heavy and Light Chains The expression of the heavy and light chains as scFv or Fab fragments is effected as described in Example 1.

2.6. Immortalization of Antigen-Specific B Lymphocytes

The immortalization is achieved by means of EBV transformation. The method is explained in some detail in Example 1.

REFERENCES

1. Mudde, G. C., et al., Antigen presentation in allergic sensitization. Immunol Cell Biol, 1996, 74(2): p. 167-173.
2. Vercelli, D., et al., To E or not to E? Can an IL-4-induced B cell choose between IgE and IgG4? Int Arch Allergy Immunol, 1998, 116(1): p. 1-4.
3. Lieby, P., et al., The clonal analysis of anticardiolipin antibodies in a single patient with primary antiphospholipid syndrome reveals an extreme antibody heterogeneity. Blood, 2001, 97(12): p. 3820-3828.
4. Wang, X. and B. D. Stollar, Human immunoglobulin variable region gene analysis by single cell RT-PCR. J Immunol Methods, 2000, 244(1-2): p. 217-225.
5. Luger E., Lamers M., Achatz-Straussberger G., Geisberger R., Inführe D., Breitenbach M., Crameri R. and Achatz G. Somatic diversity of the immunoglobulin repertoire is controlled in an isotype-specific manner. (2001) Eur. J. Immunol. 31: 2319-2330
6. Sambrook J., Fritsch E. F. and Maniatis T. (1989) Molecular Cloning, A laboratory Manual, second edition CSH Cold Spring Harbor laboratory Press, ISBN 0-87969-309-6
7. Dower W J, Miller J F, Ragsdale C W. High efficiency transformation of *E. coli* by high voltage electroporation. Nucleic Acids Res. 1988 Jul. 11; 16(13):6127-45.
8. Klimka, A., et al., An anti-CD30 single chain Fv selected by phage display and fused to *Pseudomonas* exotoxin A (Ki-4(scFv)-ETA') is a potent immunotoxin against Hodkin-derived cell line—Br J Cancer, 1999, 80(8): p. 1214-1422.
9. Barth, S., et al., (Ki-4(scFv)-ETA'), a new recombinant anti-CD30 immunotoxin with highly specific cytotoxic activity against disseminated Hodkin tumors in SCID mice. Blood, 2000, 95(12): p. 3909-3914.
10. Matthey, B., et al., Recombinant immunotoxins for the treatment of Hodkin's disease (Review). Int J Mol Med, 2000, 6(5): p. 509-514.
11. Hansen, H. P., et al., Inhibition of metalloproteinases enhances the internalization of anti-CD30 antibody Ki-3 and the cytotoxic activity of Ki-3 immunotoxin. Int J Cancer, 2002, 98(2): p. 210-215.
12. Klimka, A., et al., Human anti-CD30 recombinant antibodies by guided phage antibody selection using cell panning. Br J Cancer, 2000, 83(2): p. 252-260.
13. Tur, M. K., et al, Selection of scFv phages on intact cells under low pH conditions leads to a significant loss of insert-free phages. Biotechniques, 2001, 30(2): p. 410, 412-413.
14. Barth, S., et al., Construction and in vitro evaluation of RFT5(scFv)-ETA', a new recombinant single-chain immunotoxin with specific cytotoxicity towards $CD25^+$-Hodkins-derived cell lines. Int J Mol med, 1998, 1(1): p. 249-256.
15. Barth, S., et al., Recombinant anti-CD25 immunotoxin RFT5(scFv)-ETA' demonstrates successful elimination of disseminated human Hodkin lymphoma in SCID mice. Int J Cancer, 2000, 86(5): p. 718-724.
13. Luger, E., et al., Somatic diversity of the immunoglobulin repertoire is controlled in an isotype-specific manner. Eur J Immunol, 2001, 31(8): p. 2319-2330.

The invention claimed is:

1. A process for determining an antigen-specific V gene repertoire of immunoglobulin classes of an organism in vitro, comprising:
   (a) isolating a fraction containing B cells from a body fluid and/or tissue;
   (b) isolating B cells or their genetic material from the isolated fraction and depositing one or more of the B cells or their genetic material into a reaction vessel;
   (c) amplification of the genetic material coding variable regions of an antibody expressed by one or more of the B cells, with the amplification providing for amplification of all immunoglobulin classes in the group consisting of IgM, IgG, IgE and IgA, comprising:
      (i) performing reverse transcription reactions on the genetic material using primers comprising a sequence complementary to constant regions of light and heavy chains to obtain a cDNA amplification product;
      (ii) obtaining PCR amplificates performing PCR reactions with the cDNA amplification product as a template comprising
         performing PCR reactions with degenerate primers comprising a sequence complementary to the variable regions in the framework 1 region of the 6 gene families of the heavy chains, and/or
         performing PCR reactions with degenerate primers for the 4 gene families of the κ chains, and/or
         performing PCR reactions with degenerate primers for the 3 gene families of the λ chains, and/or
         performing PCR reactions with degenerate primers for the constant regions of the ε, γ and κ chains; and
      (iii) performing nested PCR reactions with the PCR amplificates as templates using 5' primers comprising a sequence complementary to the first 6 codons of the $V_H$ region or $V_L$ regions and 3' primers comprising a sequence complementary to nested constant regions of the κ, λ, α1, α2, γ1, γ2, γ3, γ4, μ and ε chains to obtain nested PCR amplification products;
   (d) cloning the nested PCR amplification products into a vector;
   (e) preparation of recombinant antibodies by expressing the cloned nested PCR amplification products; and
   (f) determining binding of the recombinant antibodies to recombinant and/or native antigens.

2. The process according to claim 1 comprising determining the immunological reaction profile of the organism wherein the organism's immune system is not obviously disturbed.

3. The process according to claim 2, wherein the organism is a human.

4. The process according to claim 2 comprising determining a potential of a predisposition for atopic diseases or antibody-mediated autoimmune diseases for the organism.

5. The process according to claim 1 comprising identifying the organism as having an immune function disorder and determining an immunological reaction profile of the organism.

6. The process according to claim 5, wherein the organism is a human.

7. The process according to claim 1, wherein the isolation of individual B cells comprises the following steps:
   (a) labeling of the B cells by fluorochrome-coupled antibodies, preferably with antibodies specific for at least one of CD19, CD85 and CD138, CD19, CD85, CD 138, CD10, CD20, CD21, CD22, CD23, CD24, CD27, CD37, CD38, CD39, CD40, CD72, CD73, CD74, CDw75, CDw76, CD77, CDw78, CD79, CD80, CD81, CD82, CD83, CDw84, CD85 and CD86;
   (b) selection of the labeled B cells by flow cytometry; and
   (c) depositing of one or more B cells into the reaction vessel.

8. The process according to claim 7, wherein the B cells are immortalized by EBV transformation after the isolation of the B cells and the depositing of one or more B cells into the reaction vessel.

9. The process according to claim 7, wherein the B cells are fused with myeloma cells after the isolation of the B cells and the depositing of one or more B cells into the reaction vessel.

10. The process according to claim 1, wherein the vector comprising nested PCR amplification products comprises amplificates of the $V_L$ and $V_H$ regions.

11. The process according to claim 1, wherein the determining the binding of the recombinant antibodies to antigens is effected by automated methods.

12. The process according to claim 11, wherein the determining the binding of the recombinant antibodies to antigens is effected by at least one of solid-phase coupled binding assays, flow cytometry, resonance spectrometry or chip arrays with recombinant and native antigens.

* * * * *

SEQUENCE LISTING

```
<160> NUMBER OF SEQ ID NOS: 50

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 1
aacagaggca gttccaga                                                       18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 2
tgtggccttg ttggcttg                                                       18

<210> SEQ ID NO 3
```

-continued

```
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 3
cttgcagaca cttggtgttc gtgc                                              24

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: PCR primer

<400> SEQUENCE: 4
agggygccag ggggaa                                                       16

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 5
tttacccrga gacagggaga ggc                                               23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 6
tttacccrga gacagggaga ggc                                               23

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: PCR primer

<400> SEQUENCE: 7
gcaggagacg aggggga                                                      17

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 8
tttaccggga tttacagaca c                                                 21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 9
```

```
gacmtcvwgh tsacccagtc tcc                                           23
```

<210> SEQ ID NO 10
<211> LENGTH: 23
<212> TYPE: DNA
<213> ORGANISM: Artificial Sequence
<220> FEATURE:
<223> OTHER INFORMATION: escription of Artificial Sequence: PCR primer

<400> SEQUENCE: 10

```
gacctccagh tgacccarws ycc                                           23
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 11

```
gacctccarh tsaskcagtc tcc                                           23
```

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 12

```
gakvtygtga tgacycagwc tcc                                           23
```

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 13

```
gacatcswga tgaccmagtc tcc                                           23
```

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 14

```
gacctcgtgh tgacbcagds ycc                                           23
```

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 15

```
gacatsvwgc tcacscagtc tcc                                           23
```

<210> SEQ ID NO 16
<211> LENGTH: 23
<212> TYPE: DNA
<213> ORGANISM: Artificial Sequence
<220> FEATURE:

<223> OTHER INFORMATION: Description of Artificial Sequence: PCR primer

<400> SEQUENCE: 16
tcgtttgatc tccasyykkg tcc                                           23

<210> SEQ ID NO 17
<211> LENGTH: 23
<212> TYPE: DNA
<213> ORGANISM: Artificial Sequence
<220> FEATURE:
<223> OTHER INFORMATION: escription of Artificial Sequence: PCR primer

<400> SEQUENCE: 17
tcgtttraty agtaccykkg tcc                                           23

<210> SEQ ID NO 18
<211> LENGTH: 23
<212> TYPE: DNA
<213> ORGANISM: Artificial Sequence
<220> FEATURE:
<223> OTHER INFORMATION: escription of Artificial Sequence: PCR primer

<400> SEQUENCE: 18
tcgtttgayh tscascttkg tcc                                           23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 19
cagtctswgc tgackcagcc rcc                                           23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 20
cagtctsmgc tgactcagcc wss                                           23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 21
casgytwtay tgactcaayc gcc                                           23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 22
tcctmtgwgc tgacwcarcc acc                                           23

<210> SEQ ID NO 23

```
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 23
tcktmtgarc tgactcarga ccc                                            23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 24
cagtctgtgc tgactcagsm dss                                            23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 25
acckagracg gtsasctbgg tcc                                            23

<210> SEQ ID NO 26
<211> LENGTH: 23
<212> TYPE: DNA
<213> ORGANISM: Artificial Sequence
<220> FEATURE:
<223> OTHER INFORMATION: escription of Artificial Sequence: PCR primer

<400> SEQUENCE: 26
acytargacg gtsavyttgg tcc                                            23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 27
acctarracg gtsavctkgg tcc                                            23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 28
caggtgcagc tgswgsartc kgg                                            23

<210> SEQ ID NO 29
<211> LENGTH: 23
<212> TYPE: DNA
<213> ORGANISM: Artificial Sequence
<220> FEATURE:
<223> OTHER INFORMATION: escription of Artificial Sequence: PCR primer

<400> SEQUENCE: 29
```
cagstgcakc tgcaggagtc sgg                                         23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 30
caggtgsagc tgswgsagtc hgg                                         23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 31
gaggtgcagc trcaksagts ggg                                         23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: misc_feature
<222> LOCATION: (21)..(21)
<223> OTHER INFORMATION: n is a, c, g, or t

<400> SEQUENCE: 32
gaggtgcarc tgktgsagtc ngs                                         23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 33
gaggtgcgrc tggtgsagws kgg                                         23

<210> SEQ ID NO 34
<211> LENGTH: 23
<212> TYPE: DNA
<213> ORGANISM: Artificial Sequence
<220> FEATURE:
<223> OTHER INFORMATION: escription of Artificial Sequence: PCR primer

<400> SEQUENCE: 34
caggtsaasy taagggagtc tgg                                         23

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 35
gaagaccttg gggctggtcg gggatg                                      26

<210> SEQ ID NO 36

-continued

```
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 36
atgcgacgac cacgttccca tcttg                                           25

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 37
gttctggatc aggcaggcga gggtgc                                          26

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 38
ctcgatgggg gctgggaggg ctttg                                           25

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 39
cctggtgcac aacggtgagg acg                                             23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 40
gtccgggaaa tcataagggt atc                                             23

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 41
gaggacggga ggcctttgyt ggag                                            24

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 42
```
caggagacga gggggaaaag                                                       20

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 43
gaaaacccag ctcagcccaa actccat                                               27

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 44
ccttggggct ggtcggggat g                                                     21

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 45
caggacgact gtaagatctt cacg                                                  24

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 46
ccccagaggt gctcttggag gagggt                                                26

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 47
ccgctgtgct ctcagaggtg ctcctg                                                26

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 48
ggccgctgtg cccccagagg tgctc                                                 25

<210> SEQ ID NO 49
<211> LENGTH: 25
<212> TYPE: DNA
<213> ORGANISM: Artificial Sequence
<220> FEATURE:

```
<223> OTHER INFORMATION: escription of Artificial Sequence: PCR primer

<400> SEQUENCE: 49
gcagcccagg gcggctgtgc tctcg                                              25

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 50
gaaaagggtt ggggcggatg c                                                  21
```